US009271810B2

(12) United States Patent
Solano Reina et al.

(10) Patent No.: US 9,271,810 B2
(45) Date of Patent: Mar. 1, 2016

(54) ORTHODONTIC ARCHWIRE BRACKET

(71) Applicants:José Enrique Solano Reina, Seville (ES); Asunción Mendoza Mendoza, Seville (ES); Laura Nieto Cavia, Barcelona (ES); Laurent Valat, Barcelona (ES); Josep Buisan Ferrer, Barcelona (ES); Beatriz Solano Mendoza, Seville (ES)

(72) Inventors: José Enrique Solano Reina, Seville (ES); Asunción Mendoza Mendoza, Seville (ES); Laura Nieto Cavia, Barcelona (ES); Laurent Valat, Barcelona (ES); Josep Buisan Ferrer, Barcelona (ES); Beatriz Solano Mendoza, Seville (ES)

(73) Assignees: José Enrique Solano Reina (ES); Asunción Mendoza Mendoza (ES)

( * ) Notice: Subject to any disclaimer, the term of this patent is extended or adjusted under 35 U.S.C. 154(b) by 0 days.

(21) Appl. No.: 14/465,590

(22) Filed: Aug. 21, 2014

(65) Prior Publication Data

US 2015/0017597 A1   Jan. 15, 2015

Related U.S. Application Data

(63) Continuation-in-part of application No. 14/053,541, filed on Oct. 14, 2013, now abandoned, which is a continuation-in-part of application No. 13/304,519, filed on Nov. 25, 2011, now abandoned.

(30) Foreign Application Priority Data

Nov. 25, 2010  (EP) .................................... 10380142

(51) Int. Cl.
*A61C 3/00*        (2006.01)
*A61C 7/28*        (2006.01)
*A61C 7/14*        (2006.01)

(52) U.S. Cl.
CPC .................. *A61C 7/287* (2013.01); *A61C 7/14* (2013.01)*A61C 7/141* (2013.01); *A61C 7/285* (2013.01); *A61C 2201/007* (2013.01) ;

(58) Field of Classification Search
CPC .............. A61C 7/12; A61C 7/14; A61C 7/28; A61C 7/285; A61C 7/287; A61C 2201/007
USPC ....................................................... 433/8–16
See application file for complete search history.

(56) References Cited

U.S. PATENT DOCUMENTS

| 3,721,005 | A | * | 3/1973 | Cohen ...................... A61C 7/14 433/16 |
|---|---|---|---|---|
| 4,243,387 | A | | 1/1981 | Prins |
| 5,302,121 | A | | 4/1994 | Gagin |
| 5,516,288 | A | | 5/1996 | Sichler |
| 7,431,586 | B1 | * | 10/2008 | Silverman ................ A61C 7/14 433/9 |
| 2003/0118967 | A1 | | 6/2003 | Tepper |
| 2007/0108287 | A1 | | 5/2007 | Davis |
| 2007/0134611 | A1 | | 6/2007 | Nicholson |

FOREIGN PATENT DOCUMENTS

| ES | 2232243 A1 | 5/2005 |
|---|---|---|
| WO | 2008/061218 A2 | 5/2008 |

* cited by examiner

*Primary Examiner* — Heidi M Eide
(74) *Attorney, Agent, or Firm* — Hess Patent Law Firm LLC; Robert J. Hess (57) ABSTRACT

The orthodontic archwire bracket comprises a base body (10) having a base element (11) to be fixed to a tooth and a bracket body (20) having a socket element (25) surrounded by a perimetric wall (32) including two opposed slot portions (21*a*, 21*b*) forming a slot (21) to receive an archwire. The base and bracket bodies (10, 20) are connected by a ball and socket joint coupling. The perimetric wall (32) has a slit (33) providing a gap. A control element (60) mounted on the bracket body (20) is changeable between locking and unlocking positions to expand or constrict the bracket body (20) by increasing or reducing the gap. The ball and socket joint coupling is locked by friction when the control element (50) is in the locking position and the ball and socket joint coupling is unlocked enabling relative movement in three coordinate axes when the control element (50) is in the unlocking position.

13 Claims, 7 Drawing Sheets

ORTHODONTIC ARCHWIRE BRACKET

TECHNICAL FIELD

The present invention relates to an archwire bracket applicable to orthodontic techniques which use an archwire secured to a plurality of such brackets, which are in turn fixed to several teeth of a patient, to apply a predetermined torque to said teeth and thus correct defects in the teeth. This archwire bracket is also often referred to with the term "bracket" in the orthodontics sector.

BACKGROUND OF THE INVENTION

Patent ES-A-2232243, of the same inventor as the present invention, describes an orthodontic archwire bracket including a base body with a base for being fixed to a tooth, a bracket body with a slot for the archwire, and an adjustment mechanism based on a ball and socket joint coupling between said base and bracket bodies, wherein the base body defines a socket element and the bracket body defines a ball element. The bracket body is made of a material having shape memory due to a thermal effect, such that when the two coupled bodies are at a temperature below the body temperature they are capable of mutual movement, and when they are heated to body temperature the expansion of the bracket body locks the ball and socket joint coupling in a desired position, which allows adjusting the torque and the inclination of the archwire without needing to change the bracket.

Nevertheless, a drawback of this bracket of the mentioned patent ES-A-2232243 is that the bracket body is essentially solid, so it is economically costly due to the relatively high price of the shape memory material and the impossibility of making it functional. Another drawback is that the bracket body does not include a retaining element for retaining the archwire in the corresponding slot, which forces resorting to additional elements.

U.S. Pat. No. 4,243,387 discloses an orthodontic archwire bracket including a base body having a base for being fixed to a tooth and a bracket body having a slot for the archwire. The base body and the bracket body are coupled to one another by a ball and socket joint coupling, wherein the base body has an inner spherical surface portion and the bracket body has an outer spherical surface portion. A screw inserted through an opening of the bracket body and threaded to the base body is operable to lock or unlock said ball and socket joint coupling. However, the fact that the screw head is located at the bottom of a hollow portion of the bracket body below the archwire makes it difficult to reach it with a driving tool, and also the bracket body does not include a retaining element for retaining the archwire in the slot.

International patent application WO 03/000151 discloses an orthodontic archwire bracket comprising a base to which there is fixed a plurality of parts having respective slot portions which together define a slot for the archwire and cavities between the slot portions where there are housed C-shaped latches for retaining the archwire in the slot. The latches can optionally be made of a material having shape memory. Nevertheless, this archwire bracket does not include adjustment means for varying the angular position of the archwire with respect to the base and the torque transmitted by the latter to the bracket. Furthermore, said plurality of parts imposes onerous manufacturing and assembly tasks.

DISCLOSURE OF THE INVENTION

The present invention contributes to mitigating the previous and other drawbacks by providing an orthodontic archwire bracket comprising a base body having a base element configured to be fixed to a tooth and a bracket body having a main slot configured to receive an archwire. Said base body and said bracket body are connected to one another by a ball and socket joint coupling comprising a ball element formed on the base body and a socket element formed in the bracket body. The ball and socket joint coupling allows relative rotational movement in three coordinate axes. A retaining element is connected to the bracket body to retain said archwire in said main slot, and a control element is included, which is operable to lock or unlock said ball and socket joint coupling.

The bracket body has a perimetric wall surrounding said socket element, and said main slot comprises two mutually aligned main slot portions formed in said perimetric wall at opposite sides of the socket element. The perimetric wall includes a slit providing a gap which interrupts the continuity in the ring shape of the perimetric wall, so that the bracket body can be expanded or constricted by increasing or reducing said gap provided by said slit.

The aforementioned control element is mounted on the bracket body and is changeable between a locking position and an unlocking position to expand or constrict the bracket body, hereby the ball and socket joint coupling is locked by friction force between the ball element and the socket element when the control element is in said locking position and the ball and socket joint coupling is unlocked enabling relative movement of the ball element and the socket element when the control element is in said unlocking position.

In a first embodiment, the socket element of the bracket body has an interference fit with the ball element of the base body, so that said interference fit locks the ball and socket joint coupling by friction force when the bracket body is in a rest condition, i.e., with no external expanding forces applied thereon. The ball element and the socket element are dimensioned such that in the rest condition the friction force is strong enough to lock the ball and socket joint against the forces applied by the archwire to the bracket body in order to correct the position of the teeth. In this case, the control element is configured to expand the bracket body by elastic deformation thereof from said rest condition to an expanded condition in which the ball and socket joint coupling is unlocked when the control element is changed to said unlocking position.

For example, the control element comprises a control shaft inserted in said gap provided by said slit in the perimetric wall of the bracket body. The mentioned control shaft has a width equal or lesser than a distance between opposite surfaces of the slit in said rest condition. The control shaft has one or more eccentric portions protruding from one side thereof, with said eccentric portion having a width greater than said distance between said opposite surfaces of the slit in the rest condition, so that when the control shaft is turned a predetermined angle about its own axis to the unlocking position the one or more eccentric portions press the opposite surfaces of the slit away from one another to expand the bracket body to the expanded condition thereby unlocking the ball and socket joint coupling.

Preferably, the control element further comprises a head at one end of the control shaft, and said head includes a grip element configured to be gripped by a tool to rotate the control shaft. Also preferably, the control element has at least two spaced apart eccentric portions protruding from one side of the control shaft and the bracket body has at least one retaining lug protruding from at least one of the opposite surfaces of the slit. Said retaining lug is interposed between said two spaced apart eccentric portions to axially retain the control element to the bracket body.

Given that the control element is axially retained to the bracket body, in one variant of the first embodiment the aforementioned retaining element is movably connected to the bracket body by the head of the control element. For example, the head of the control element wider than the control shaft and is located at a higher level than said upper edge of the perimetric wall of the bracket body, and the retaining element has a guide channel configured to receive the head of the control element and retaining rims partially closing said guide channel and configured to receive the control shaft of the control element, so that the head and the control shaft can slide along the guide channel in a radial direction between closed and open positions, and the head is retained in the guide channel by the retaining rims in an axial direction. Said retaining rims are interposed between the head and the upper edge of the perimetric wall.

In the closed position, the retaining element is located on an upper edge of the perimetric wall of the bracket body closing an entrance of the main slot portions of the main slot, and in the open position, the retaining element is withdrawn so that said entrance of the main slot portions is open. Preferably, the guide channel of the bracket body has an open end which is adjacent to the slit when the retaining element is in the closed position and an end stop at an opposite end thereof which is adjacent to the slit when the retaining element is in the open position. Said end stop interferes with the control shaft when the retaining element is in the open position limiting movement thereof in an opening direction.

The bracket body has preferably one or more securing tabs adjacent to one side thereof opposite the slit and the retaining element has one or more securing protrusions adjacent to said end stop of the guide channel. Said one or more securing tabs of the bracket body interlock with said one or more securing protrusions of the retaining element when the retaining element is at the closed position. This secures the retaining element in the closed position and limits the movement thereof in a closing direction.

The retaining element further has an elastic tab adjacent to the one or more securing protrusions, and said elastic tab has a retaining lip which snap fits on a side edge of the of the perimetric wall of the bracket body when the retaining element is at the closed position.

Preferably, the base element and the ball element of the base body are attached to one another by releasable attaching means, such as, for example, a threaded coupling or a snap fit coupling. In one variant of the first embodiment, said releasable attaching means comprise a screw threaded shaft formed in the base element and a corresponding screw threaded hole formed in the ball element.

In a second embodiment, the socket element of the bracket body has a loose fit with the ball element of the base body, said loose fit keeping the ball and socket joint coupling unlocked when the bracket body is in a rest condition i.e., with no external constricting forces applied thereon. In this case, the control element is configured to constrict the bracket body by elastic deformation thereof from said rest condition to a tightened condition in which the ball and socket joint coupling is locked by friction force when the control element is changed to said locking position. The ball element and the socket element are dimensioned such that in the tightened condition the friction force is strong enough to lock the ball and socket joint against the forces applied by the archwire to the bracket body in order to correct the position of the teeth.

For example, the control element is a control ring made of a material having shape memory fit around on an outer perimetric surface of the perimetric wall of the bracket body, wherein said material having shape memory maintains an original shape at a first temperature equivalent to body temperature and acquires a deformable state at a second temperature below body temperature. When the material having shape memory is at said first temperature, said control ring has a smaller inner diameter than an outer diameter of said outer perimetric surface of the bracket body in said rest condition. In general, the control ring is heated to the first temperature when the orthodontic archwire bracket is installed in the mouth of a patient.

Optionally, in the second embodiment the retaining element is rotationally coupled to the bracket body about a rotation axis parallel to the main slot, and is movable between an open position, at which said retaining element allows the archwire to be inserted into and removed from the main slot, and a closed position, at which the retaining element retains the archwire in the main slot. To this end, the bracket body has for example guide lugs guiding rotational movements of the retaining element between said open and closed positions, and the retaining element has a retaining portion which, when the retaining element is in the closed position, engages a pin attached to opposite surfaces of the slit of the bracket body spanning said gap.

With the described embodiments, the orthodontic archwire bracket of the present invention allows performing adjustments in the torque imparted by the archwire to the tooth through the bracket and in the angular position of the archwire with respect to the base element of the bracket in three coordinate axes as a result of the spherical ball and socket joint coupling and the control element for locking and unlocking same. Furthermore, the archwire bracket of the present invention incorporates a retaining element for retaining the archwire in the main slot without needing to use additional elements. This allows reducing the general volume of the bracket, reducing the total number of separate parts and facilitating the labor of the orthodontist.

BRIEF DESCRIPTION OF THE DRAWINGS

The previous and other features and advantages will be more fully understood from the following detailed description of several exemplary embodiments with reference to the attached drawings, in which.

DETAILED DESCRIPTION OF EXEMPLARY EMBODIMENTS

With reference first to FIGS. 1 to 13, a first embodiment of the orthodontic archwire bracket according to the present invention is described, which comprises a base body 10 having a base element 11 configured to be fixed to a tooth and a bracket body 20 having a main slot 21 configured to receive an archwire 30. The base body 10 and the bracket body 20 are connected to one another by a ball and socket joint coupling comprising a ball element 15 having an outer spherical surface 14 formed on the base body 10 and a socket element 25 having an inner spherical surface 24 formed in the bracket body 20. The ball and socket joint coupling allows rotational movements of the bracket body 20 with respect to the base body 10 about three coordinate axes.

Figure 3:
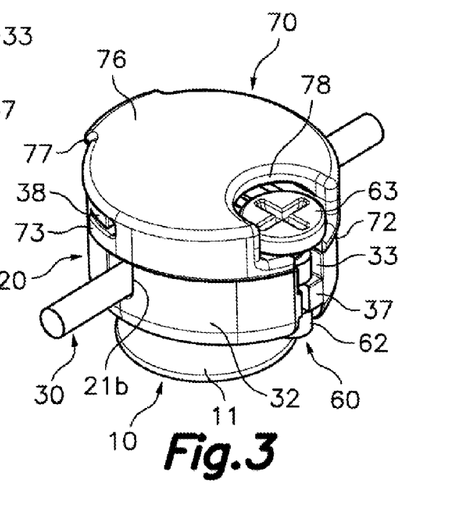
FIG. 3 is a perspective view of the orthodontic archwire bracket according to the first embodiment once assembled and with a portion of the archwire retained thereto by a retaining element in a closed position.

The bracket body 20 has a perimetric wall 32 surrounding said socket element 25, and said perimetric wall 32 includes a slit 33 providing a gap that confers certain elasticity to the bracket body 20. The main slot 21 is comprised of two mutually aligned main slot portions 21a, 21b formed in the perimetric wall 32 at opposite sides of the socket element 25. The slit 33 is formed in one side of the perimetric wall 32 intermediate the two mutually aligned main slot portions 21a, 21b. A retaining element 70 is movably connected to the bracket body 20 to retain the archwire 30 in the main slot 21, as shown in FIG. 3.

The ball element 15 of the base body 10 comprises a secondary slot 16 aligned with the main slot portions 21a, 21b of the main slot 21 of the bracket body 20 in order to give room for the archwire 30. This secondary slot 16 of the base body 10 is larger than the main slot portions 21a, 21b of the main slot 21 of the bracket body 20 in a degree sufficient to allow rotational movements of the bracket body 20 together with the archwire 30 retained in the main slot 21 thereof with respect to the base body 10 about the three coordinate axes.

A control element 60 is mounted on the bracket body 20 such that it is operable to lock or unlock said ball and socket joint coupling. In this first embodiment, the inner spherical surface 24 of the socket element 25 of the bracket body 20 has an interference fit with the outer spherical surface 14 of the ball element 15 of the base body 10. This interference fit is enough for locking the ball and socket joint coupling by friction force when the bracket body 20 is in a rest condition, i.e., with no external expanding forces applied thereon, and the control element 60 is configured to expand the bracket body 20 by elastic deformation thereof from said rest condition to an expanded condition in which the ball and socket joint coupling is unlocked when the control element 60 is changed to said unlocking position.

The control element 60 comprises a control shaft 61 inserted in the gap provided by the slit 33 in the perimetric wall 32 of the bracket body 20. The control shaft 61 has a general width equal or lesser than a distance between opposite surfaces of the slit 33 when the bracket body is in said rest condition. The control shaft 61 has two spaced apart eccentric portion 62 protruding from one side thereof. Said eccentric portions 62 have a width greater than the mentioned distance between opposite surfaces of the slit 33 in the rest condition. Thus, when the control shaft 61 is turned a predetermined angle about its own axis to the unlocking position, the eccentric portions 62 press said on the opposite surfaces of the slit 33 moving them away from one another to increase the gap provided by the slit and expand the bracket body 20 to the expanded condition.

Therefore, when the control shaft 61 is in the unlocking position, the ball and socket joint coupling is unlocked and relative rotational movement between the ball element 15 of the base body and the socket element 25 of the bracket body 20 is allowed in three coordinate axes.

The bracket body 20 comprises retaining lugs 37 protruding from the opposite surfaces of the slit 33, and said retaining lugs 37 are interposed between the two spaced apart eccentric portions 62 of the control shaft 61, so that the control element 60 is axially retained to the bracket body 20 while it is allowed to rotate about its own axis. The control element 60 further comprises a head 63 at one end of the control shaft 61, and said head 63 includes a grip element 64 configured to be gripped by a driving tool to rotate the control shaft 61.

In this first embodiment, given that the control element 60 is axially retained to the bracket body 20, the head 63 of the retaining element 60 is used to movably connect the retaining element 70 to the bracket body 20 so that the retaining element 70 is movable between a closed position (FIGS. 3-6), in which the retaining element 70 is located on an upper edge 32a of the perimetric wall 32 of the bracket body 20 closing the entrances of the main slot portions 21a, 21b of the main slot 21, and an open position (FIG. 13), in which said entrance of the main slot portions 21a, 21b is open.

To this end, the head 63 of the control element 60 is wider than the control shaft 61 and is located at a higher level than said upper edge 32a of the perimetric wall 32 of the bracket body 20, and the retaining element 70 has the shape of a lid for the bracket body 20 comprising a guide channel 71 configured to receive the head 63 of the control element 60 and retaining rims 72 partially closing said guide channel 17. Said retaining rims 72 protrude towards one another from both sides of the guide channel 71 and all along the guide channel 71 leaving between them a slot dimensioned to receive the control shaft 61 of the control element 60, so that the retaining rims 72 are interposed between the head 63 of the control element 60 and the upper edge 32a of the perimetric wall 32 of the bracket body 20.

With this construction, the retaining element 70 can be slid to the bracket body 20 in a radial direction between said closed and open positions guided by the head 63 and the control shaft 61 of the control element 60 sliding along the guide channel 71, while it is axially retained to the bracket body 20 by the retaining rims 72 preventing the head 63 from moving in the guide channel 71 in an axial direction.

Figure 9:
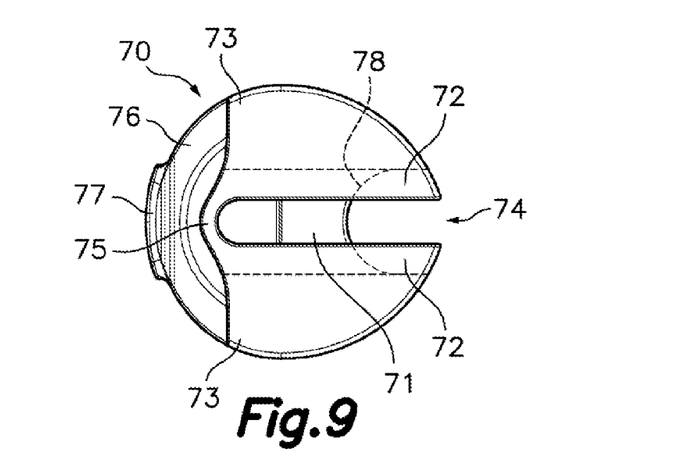
FIG. 9 is a bottom plan view showing a lower side of the retaining element of the orthodontic archwire bracket according to the first embodiment.
Figure 13:
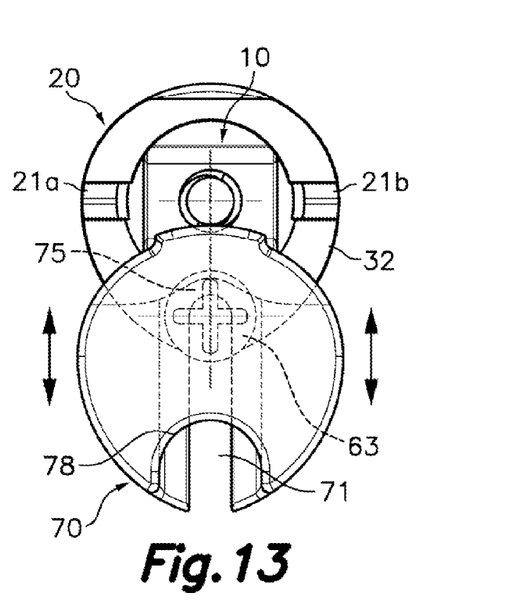
FIG. 13 is a plan view of the orthodontic archwire bracket according to the first embodiment, with the retaining element in an open position.
Figure 14:
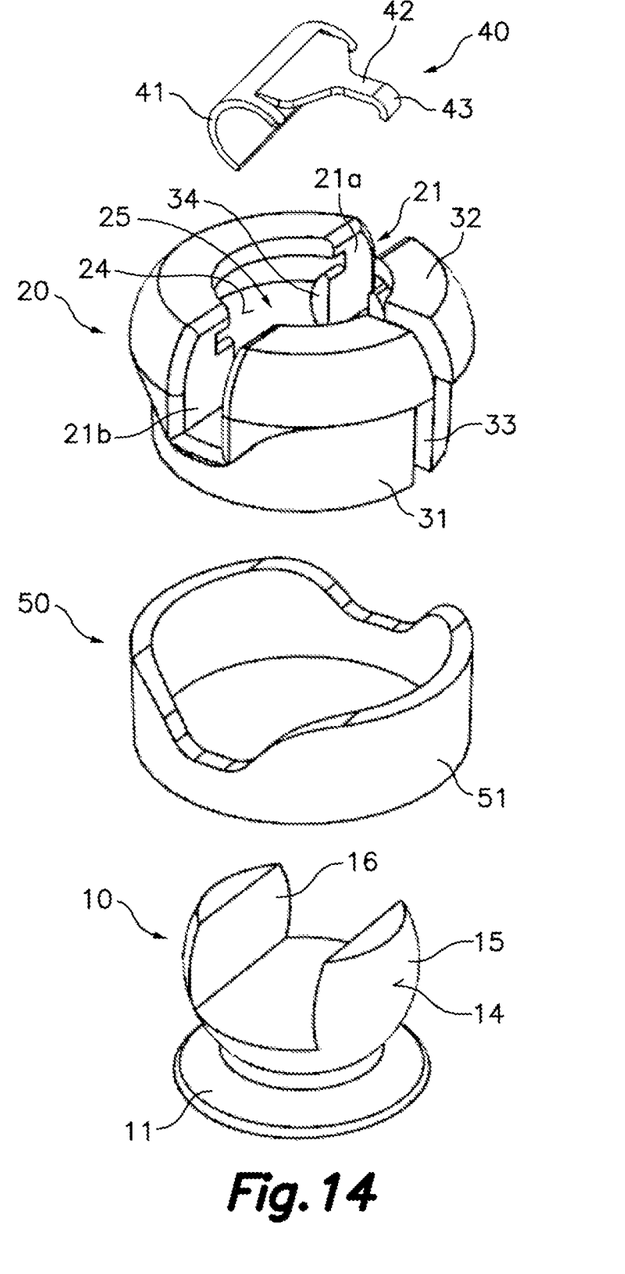
FIG. 14 is an explosion perspective view of an orthodontic archwire bracket according to a second embodiment of the present invention.
Figure 15:
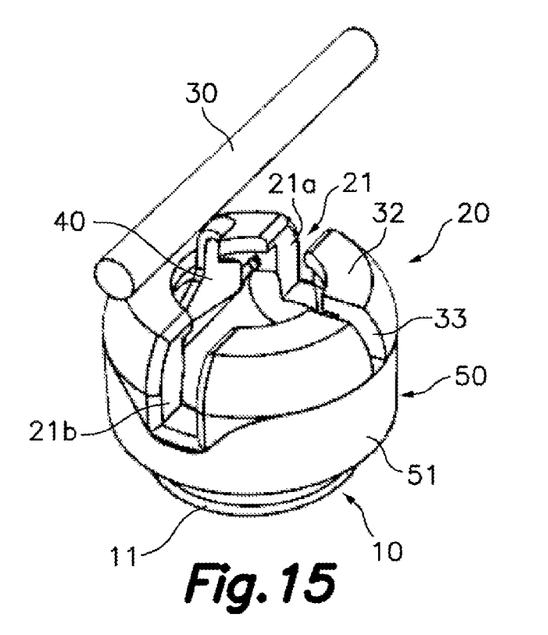
FIG. 15 is a perspective view of the orthodontic archwire bracket according to the second embodiment once assembled, with a retaining element in an open position, and with a portion of the archwire about to be inserted into the bracket.
Figure 16:
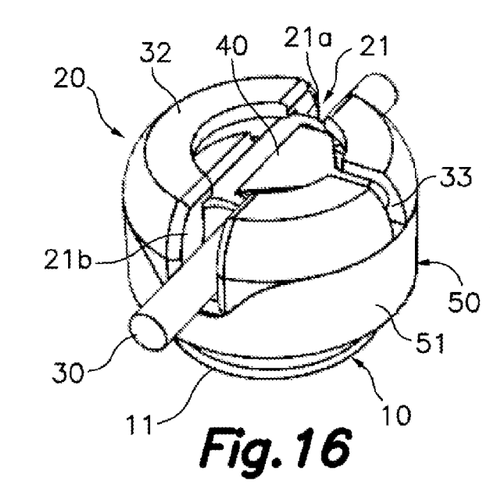
FIG. 16 is a perspective view of the orthodontic archwire bracket according to the second embodiment once assembled, with the retaining element in a closed position retaining the portion of the archwire in the bracket.
Figure 17:
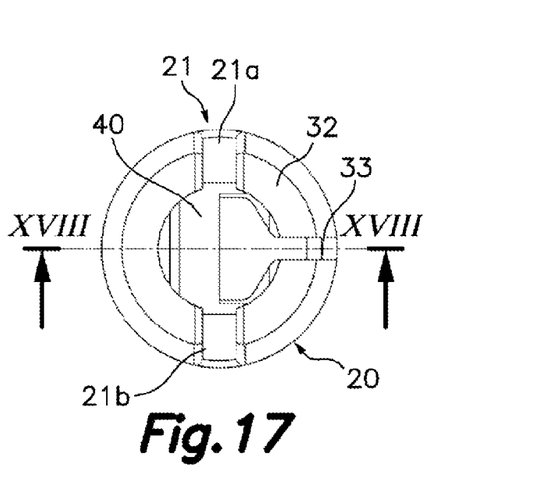
FIG. 17 is a plan view of the orthodontic archwire bracket according to the second embodiment, with the retaining element in the closed position.

As shown in FIG. 9, the guide channel 71 of the retaining element 70 has an open end 74 at one end thereof and an end stop 75 at an opposite end thereof. The open end 74 is adjacent to the slit 33 of the bracket body 20 when the retaining element 70 is in the closed position (FIGS. 4 and 5) and an end stop 75 is adjacent to the slit 33 of the bracket body 20 when the retaining element 70 is in the open position (FIG. 13).

Figure 10:
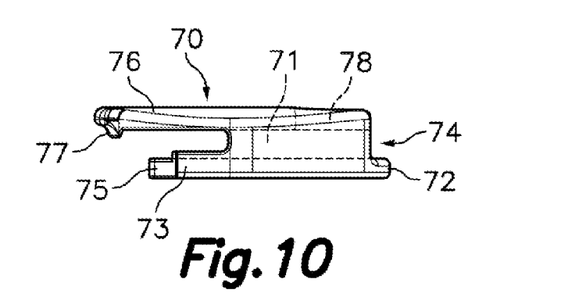
FIG. 10 is a side view of the retaining element of the orthodontic archwire bracket according to the first embodiment.

The retaining element 70 has a pair of securing protrusions 73 adjacent to said end stop 75 of the guide channel 71, as better shown in FIG. 10, and the bracket body 20 has at least a pair of corresponding securing tabs 38 adjacent to one side thereof opposite the slit 33. The securing protrusions 73 of the retaining element 70 interlock with the securing tabs 38 of the bracket body 20 when the retaining element 70 is at the closed position (see FIGS. 3 and 5) thereby securing the axial retention of the retaining element 70 to the bracket body 20 at one thereof end spaced apart from the control element 60 when the retaining element 70 is in the closed position.

Figure 4:
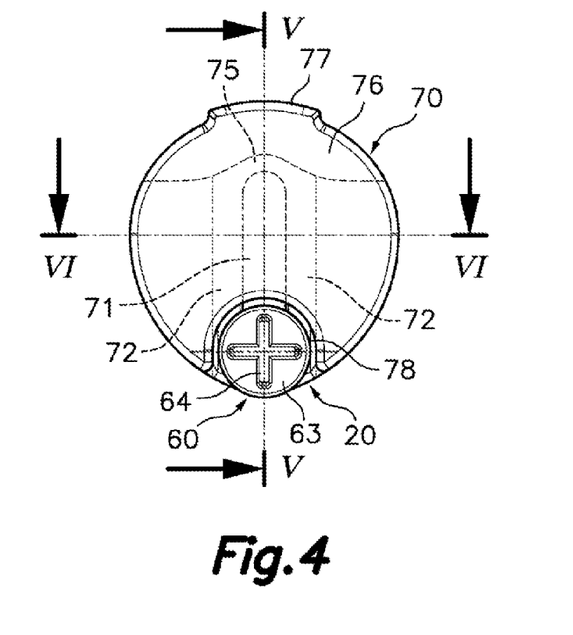
FIG. 4 is a plan view of the orthodontic archwire bracket according to the first embodiment, with the retaining element in the closed position.
Figure 5:
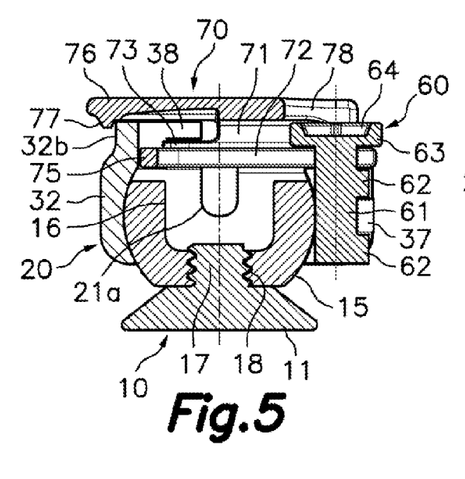
FIG. 5 is a cross-sectional view taken along the section line V-V of FIG. 4.
Figure 6:
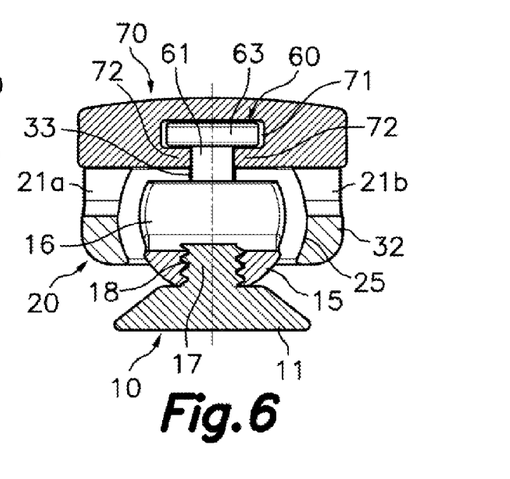
FIG. 6 is a cross-sectional view taken along the section line VI-VI of FIG. 4.

As better shown in FIGS. 5, 9 and 10, the retaining element 70 further includes an elastic tab 76 adjacent to the securing protrusions 73 and an access notch 78 adjacent to the open end 74 of the guide channel 71. The said elastic tab 76 has a retaining lip 77 which snap fits on a side edge 32b of the perimetric wall 32 of the bracket body 20 (FIG. 5) when the retaining element 70 is at the closed position. The access notch 78 gives access to the head 63 and grip element 64 of the control element 60 when the retaining element 70 is at the closed position (FIG. 4). Furthermore, when the retaining element 70 is at the closed position, it covers a hollow portion of the bracket body 20 and base body 10 assembly thanks to the lid shape thereof.

Figure 1:
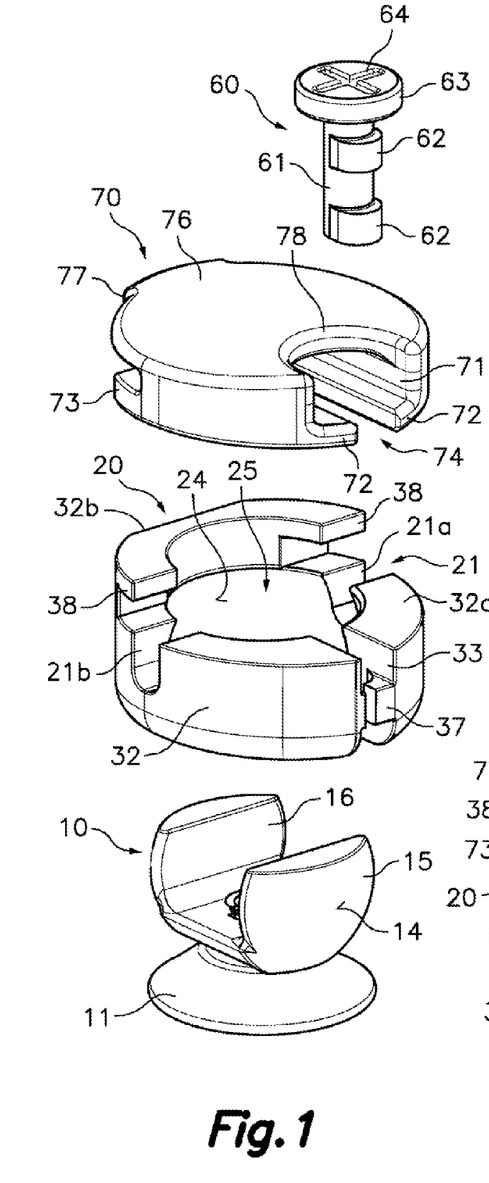
FIG. 1 is an explosion perspective view of an orthodontic archwire bracket according to a first embodiment of the present invention.
Figure 2:
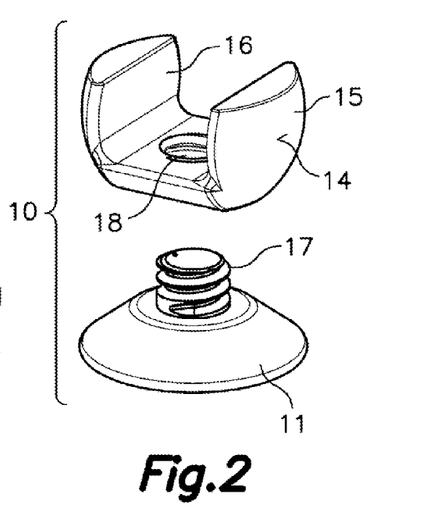
FIG. 2 is an explosion perspective view of a base body included in the orthodontic archwire bracket according to the first embodiment.

FIG. 2 shows the base body 10 embodied in two separable parts, with one part comprising the base element 11 and the other part comprising the ball element 15, which are attached to one another by releasable attaching means. More specifically, the base element 11 includes a screw threaded shaft 17 protruding therefrom and the ball element 15 has a corresponding screw threaded hole 18 formed therein to which is coupled the screw threaded shaft 17.

Only by way of example, the retaining element 70 can be made of a polymer having a good resistance to chemical and thermal attack, such as polyphenylene sulfide (PPS), and the base body 10, the bracket body 20 and the control element 60 can be made of stainless steel.

Figure 7:
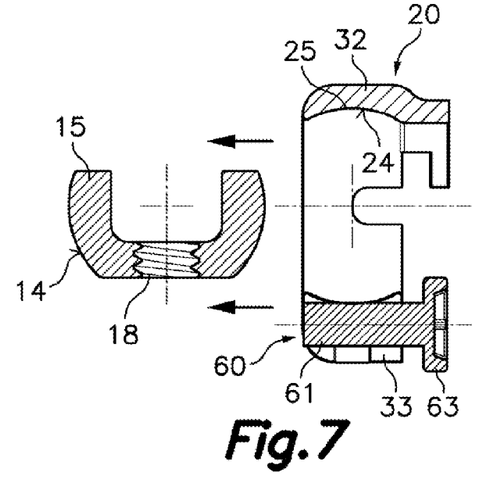
FIGS. 7 and 8 are cross-sectional views showing different steps of a coupling operation to couple a ball element of the base body to a socket element of the bracket body in the orthodontic archwire bracket according to the first embodiment.
Figure 8:
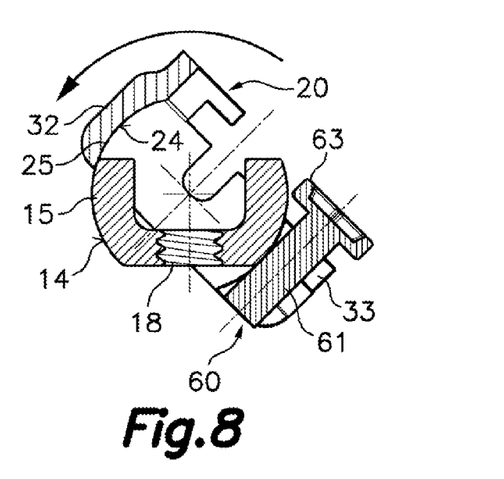

FIGS. 7 and 8 show a procedure to assemble the ball element 15 of the base body 10 and the socket element 25 of the bracket body 20. Firstly, the control element 60 is installed in the slit 33 of the bracket body 20 and turned to the unlocking position to expand the bracket body 20. Then, the ball element 15 alone is introduced into the socket element 25 of the bracket body 20 while maintaining a central axis of the ball element 15 perpendicular to a central axis of the socket element 25 (FIG. 7). Finally, the bracket body 20 is rotated with respect to the ball element 15 (FIG. 8) and the base element 11 of the base body 10 can be attached to the ball element 15 by coupling the screw threaded shaft 17 to the screw threaded hole 18.

Figure 11:
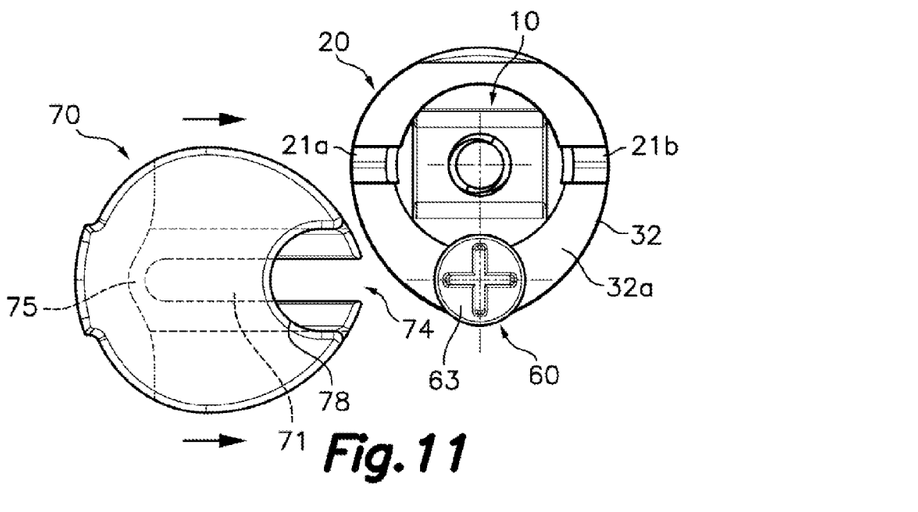
FIGS. 11 and 12 are plane views showing different steps of a coupling operation to couple the retaining element to the bracket body in the orthodontic archwire bracket according to the first embodiment.
Figure 12:
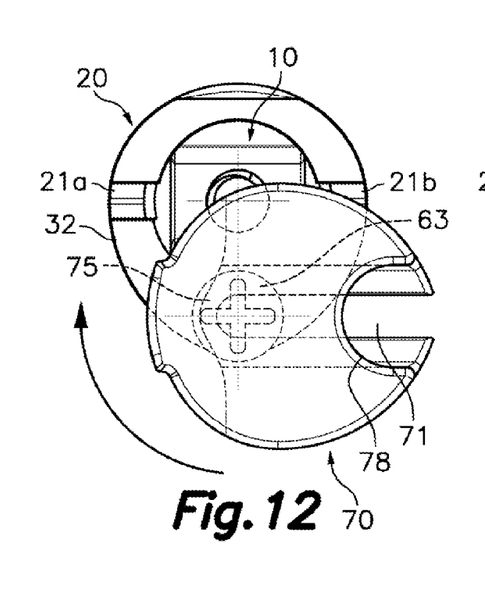

FIGS. 11-13 show a procedure to assemble the retaining element 70 and the bracket body 20. Firstly, the control element 60 is installed in the bracket body 20 and the retaining element 70 is positioned with the guide channel 71 parallel to the main slot portions 21a, 21b of the main slot 21 of the bracket body 20 (FIG. 11) and. Then, the guide channel 71 is coupled to the head 63 of the control element 60 and the retaining element 70 is slit in said direction parallel to the main slot portions 21a, 21b of the main slot 21 of the bracket body 20 until the control shaft 61 of the control element 60 makes contact with the end stop 75 of the guide channel 71 (FIG. 12). Finally, the retaining element 70 is rotated about the axis of the control shaft 61 until reaching the open position (FIG. 13). From the open position shown in FIG. 13, the retaining element 70 can be slidingly moved to the closed position (FIG. 4), and vice versa, as explained above.

FIGS. 14 to 19 show a second embodiment of the orthodontic archwire bracket according to the present invention, which like the first embodiment comprises a base body 10 and a bracket body 20 connected to one another by a ball and socket joint coupling. The base body 10 has a base element 11 configured to be fixed to a tooth and a ball element 15, and the bracket body 20 has a main slot 21 configured to receive an archwire 30 (FIGS. 15 and 16): and a socket element 25 configured to receive the ball element 15 of the base body 10. The orthodontic archwire bracket further comprises a retaining element 40 movably connected to the bracket body 20 to retain the archwire 30 in the main slot 21 and a control element 50 operable to lock or unlock the ball and socket joint coupling.

The bracket body 20 has a perimetric wall 32 surrounding the socket element 25, and the perimetric wall 32 includes a slit 33 providing a gap that confers certain elasticity to the bracket body 20. The main slot 21 comprises two mutually aligned main slot portions 21a, 21b formed in the perimetric wall 32 at opposite sides of the socket element 25, and the slit 33 is formed in one side of the perimetric wall 32 intermediate the two mutually aligned main slot portions 21a, 21b.

The ball element 15 of the base body 10 comprises a secondary slot 16 aligned with the main slot portions 21a, 21b of the main slot 21 of the bracket body 20 in order to give room for the archwire 30. This secondary slot 16 of the base body 10 is larger than the main slot portions 21a, 21b of the main slot 21 of the bracket body 20 in a degree sufficient to allow rotational movements of the bracket body 20 together with the archwire 30 retained in the main slot 21 thereof with respect to the base body 10 about three coordinate axes.

However, in this second embodiment, the inner spherical surface 24 of the socket element 25 of the bracket body 20 has a loose fit with the outer spherical surface 14 of the ball element 15 of the base body 10 when the bracket body 20 is in a rest condition, i.e., with no external constricting forces applied thereon, and said loose fit keeps the ball and socket joint coupling unlocked in the rest condition. The control element 50 is configured to constrict the bracket body 20 by elastic deformation thereof from said rest condition to a tightened condition in which the ball and socket joint coupling is locked by friction force when the control element 50 is changed to a locking position.

The control element 50 is in the form of a control ring 51 made of a material having shape memory, such as for example a nickel-titanium alloy, which maintains an original shape at a first temperature equivalent to body temperature and acquires a deformable state at a second temperature below body temperature, while the bracket body 20 can be made of another material, such as a polymeric material, for example polyether ether ketone (PEEK).

Figure 18:
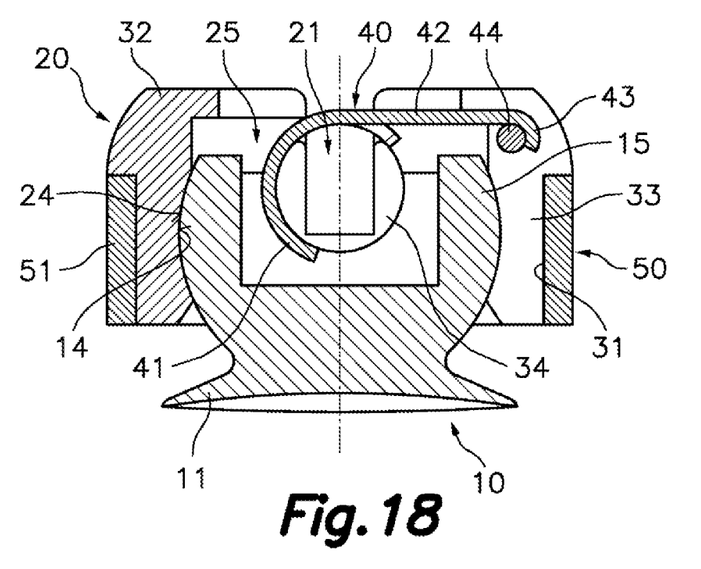
FIG. 18 is a cross-sectional view taken along the section line XVIII-XVIII of FIG. 17.
Figure 19:
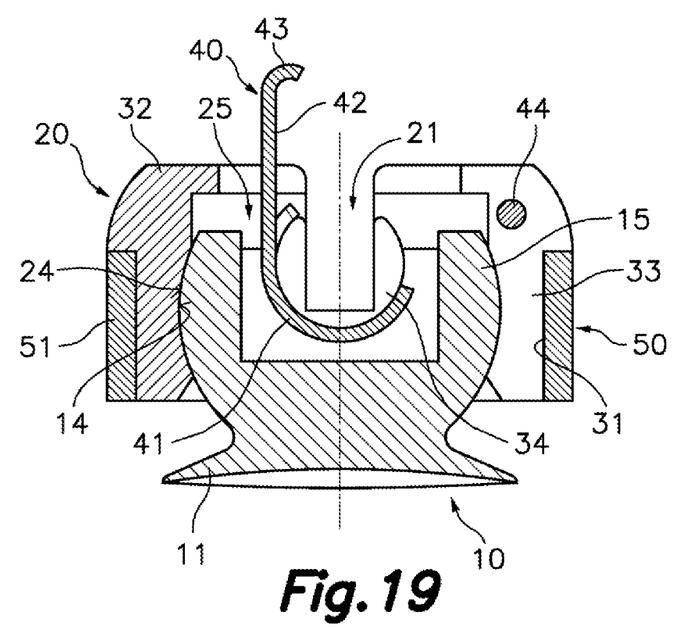
FIG. 19 is a cross-sectional view similar to FIG. 18 with the retaining element in an open position.

As better shown in FIGS. 18 and 19, the perimetric wall 32 of the bracket body 20 has an outer perimetric recess 31 providing an outer perimetric surface, and the control ring 51 is fit around on said outer perimetric surface of the outer perimetric recess 31 of the bracket body 20. The control ring 51 is dimensioned so that, when the material having shape memory is at said first temperature, the control ring 51 acquires said locking position in which it has a smaller inner diameter than an outer diameter of the outer perimetric surface of the bracket body 20 in said rest condition, and when the material having shape memory is at said second temperature, the control ring 51 acquires an unlocking position in which it has an inner diameter equal or greater than the outer diameter of the outer perimetric surface of the bracket body 20 in said rest condition.

Thus, the ball and socket joint coupling allows relative movements between the bracket body 20 and the base body 10 when the control ring 51 is at said second temperature at which the material having shape memory part is deformable and the bracket body 20 is at the rest condition. However, when the control ring 51 is heated to said first temperature at which the material having shape memory recovers its original shape, the control ring 51 constricts the bracket body 20 reducing the gap provided by the slit 33 so that the ball and socket joint coupling is locked by friction force between the outer spherical surface 14 of the ball element 15 of the base body 10 and the inner spherical surface 24 of the socket element 25 of the bracket body 20.

The aforementioned retaining element 40 is movable between an open position (FIGS. 15 and 19), at which the retaining element 40 allows the archwire 30 to be inserted into and removed from the main slot 21, and a closed position (FIGS. 16, 17 and 18), at which the retaining element 40 retains the archwire 30 in the main slot 21. Guiding means are provided to guide the movements of the retaining element 40 between said open and closed positions.

In the example shown in FIGS. 14 to 19, the retaining element 40 is made for example of contoured sheet metal and has a concave part-cylindrical portion 41 and a retaining arm 42 ending in a bent retaining portion 43. In use, opposite ends of said concave part-cylindrical portion 41 of the retaining element 40 are rotationally coupled to guide lugs 34 formed in an inner surface of the perimetric wall 32 of the bracket body 20 and symmetrically arranged at both sides of the main slot portions 21a, 21b forming the main slot 21. In the closed position, the retaining arm 42 of the retaining element 40 is lied on the archwire and inserted in said gap provided by the slit 33 in the perimetric wall 32 of the bracket body 20, and said retaining portion 43 of the retaining arm 42 engages a pin 44 attached to attached to opposite surfaces of the slit 33 of the bracket body 20 spanning said gap.

A person skilled in the art will be able to think of modifications, variations and combinations from the embodiments shown and described without departing from the scope of the present invention as it is defined in the attached claims.

The invention claimed is:

1. An orthodontic archwire bracket, comprising:
a base body having a base element configured to be fixed to a tooth and a bracket body having a main slot configured to receive an archwire, said base body and said bracket body being connected to one another by a ball and socket joint coupling comprising a ball element formed on the base body and a socket element formed in the bracket body;
a retaining element connected to said bracket body to retain said archwire in said main slot;
and a control element operable to lock or unlock said ball and socket joint coupling,
wherein:
the bracket body has a perimetric wall surrounding said socket element, said main slot comprising two mutually aligned main slot portions formed in said perimetric wall at opposite sides of the socket element;
the perimetric wall includes a slit providing a gap;
said control element is mounted on the bracket body and changeable between a locking position and an unlocking position to expand or constrict the bracket body by increasing or reducing said gap provided by said slit, hereby the ball and socket joint coupling is locked by friction force between said ball element and the socket element when the control element is in said locking position and the ball and socket joint coupling is unlocked enabling relative rotational movement of the ball element and the socket element in three coordinate axes when the control element is in said unlocking position.

2. The orthodontic archwire bracket according to claim 1, wherein the socket element of the bracket body has an interference fit with the ball element of the base body when the bracket body is in a rest condition, said interference fit locking the ball and socket joint coupling by friction force when the bracket body is in said rest condition and the control element is in said locking position, and the control element is configured to expand the bracket body by elastic deformation thereof from said rest condition to an expanded condition in which the ball and socket joint coupling is unlocked when the control element is changed from the locking position to said unlocking position.

3. The orthodontic archwire bracket according to claim 2, wherein the control element comprises a control shaft inserted in said gap provided by said slit in the perimetric wall of the bracket body, said control shaft has a width equal or lesser than a distance between opposite surfaces of the slit in said rest condition, and the control shaft has at least one eccentric portion protruding from one side thereof, said eccentric portion having a width greater than said distance between opposite surfaces of the slit in the rest condition, the eccentric portion pressing said opposite surfaces of the slit away from one another to expand the bracket body to the expanded condition when the control shaft is turned a predetermined angle about its own axis to the unlocking position.

4. The orthodontic archwire bracket according to claim 3, wherein the control element further comprises a head at one end of the control shaft, said head including a grip element configured to be gripped by a tool to rotate the control shaft.

5. The orthodontic archwire bracket according to claim 4, wherein the control element has at least two spaced apart eccentric portions protruding from one side of the control shaft and at least one retaining lug protruding from at least one of the opposite surfaces of the slit is interposed between said two spaced apart eccentric portions to axially retain the control element to the bracket body, and said retaining element is movably connected to the bracket body by the head of the control element.

6. The orthodontic archwire bracket according to claim 5, wherein the retaining element is movable between a closed position, in which the retaining element is located on an upper edge of the perimetric wall of the bracket body closing an entrance of the main slot portions of the main slot, and an open position, in which said entrance of the main slot portions is open.

7. The orthodontic archwire bracket according to claim 6, wherein the head of the control element wider than the control shaft and is located at a higher level than said upper edge of the perimetric wall of the bracket body, and the retaining element has a guide channel configured to receive the head of the control element and retaining rims partially closing said guide channel and configured to receive the control shaft of the control element, said retaining rims being interposed between the head and the upper edge of the perimetric wall, so that the head and the control shaft can slide along the guide channel in a radial direction between said closed and open positions, and the head is retained in the guide channel by the retaining rims in an axial direction.

8. The orthodontic archwire bracket according to claim 7, wherein the guide channel of the retaining element has an open end which is adjacent to the slit of the bracket body when the retaining element is in the closed position and an end stop at an opposite end thereof which is adjacent to the slit of the bracket body when the retaining element is in the open position.

9. The orthodontic archwire bracket according to claim 8, wherein the bracket body has at least one securing tab adjacent to one side thereof opposite the slit, and the retaining element has at least one securing protrusion adjacent to said end stop of the guide channel which interlocks with said at least one securing tab of the bracket body when the retaining element is at the closed position.

10. The orthodontic archwire bracket according to claim 9, wherein the retaining element has an elastic tab adjacent to said at least one securing protrusion, said elastic tab having a retaining lip which snap fits on a side edge of the perimetric wall of the bracket body when the retaining element is at the closed position.

11. The orthodontic archwire bracket according to claim 3, wherein the ball element of the base body comprises a secondary slot aligned with the main slot portions of the main slot of the bracket body, said secondary slot being larger than the main slot portions of the main slot in a degree sufficient to allow rotational movements of the bracket body together with the archwire retained in the main slot with respect to the base body about three coordinate axes.

12. The orthodontic archwire bracket according to claim 1, wherein the base element and the ball element of the base body are attached to one another by releasable attaching means.

13. The orthodontic archwire bracket according to claim 12, wherein said releasable attaching means comprise a screw threaded shaft formed in the base element and a corresponding screw threaded hole formed in the ball element.

\* \* \* \* \*